US010493094B2

(12) United States Patent
Diehn et al.

(10) Patent No.: US 10,493,094 B2
(45) Date of Patent: Dec. 3, 2019

(54) ADVANCED FUNCTIONAL BIOCOMPATIBLE POLYMER PUTTY USED AS A HEMOSTATIC AGENT FOR TREATING DAMAGED TISSUE AND CELLS

(71) Applicants: GEL-E, Inc., College Park, MD (US); University of Maryland, College Park, College Park, MD (US); The General Hospital Corporation, Boston, MA (US)

(72) Inventors: Kevin Diehn, Towson, MD (US); Matthew Dowling, College Park, MD (US); Srinivasa R. Raghavan, Silver Spring, MD (US); David R. King, Boston, MA (US)

(73) Assignees: GEL-E, Inc., College Park, MD (US); University of Maryland, College Park, College Park, MD (US); The General Hospital Corporation, Boston, MA (US)

(*) Notice: Subject to any disclaimer, the term of this patent is extended or adjusted under 35 U.S.C. 154(b) by 0 days.

(21) Appl. No.: 15/443,062

(22) Filed: Feb. 27, 2017

(65) Prior Publication Data
US 2017/0326171 A1    Nov. 16, 2017

Related U.S. Application Data

(63) Continuation of application No. 14/208,820, filed on Mar. 13, 2014, now Pat. No. 9,616,088.

(60) Provisional application No. 61/779,706, filed on Mar. 13, 2013.

(51) Int. Cl.
*A61K 31/765* (2006.01)
*A61K 31/734* (2006.01)
*A61K 38/39* (2006.01)
*A61K 31/717* (2006.01)
*A61K 31/722* (2006.01)

(52) U.S. Cl.
CPC .......... *A61K 31/734* (2013.01); *A61K 31/717* (2013.01); *A61K 31/722* (2013.01); *A61K 38/39* (2013.01)

(58) Field of Classification Search
None
See application file for complete search history.

(56) References Cited

U.S. PATENT DOCUMENTS

| | | | |
|---|---|---|---|
| 4,394,373 A | 7/1983 | Malette et al. | |
| 4,532,134 A | 7/1985 | Malette et al. | |
| 4,572,906 A | 2/1986 | Sparkes et al. | |
| 4,752,466 A | 6/1988 | Saferstein et al. | |
| 4,895,724 A | 1/1990 | Cardinal et al. | |
| 5,128,136 A | * 7/1992 | Bentley | A01N 59/12 424/443 |
| 5,243,094 A | 9/1993 | Borg | |
| 5,426,182 A | 6/1995 | Jenkins et al. | |
| 5,623,064 A | 4/1997 | Voumakis et al. | |
| 5,624,679 A | 4/1997 | Voumakis et al. | |
| 5,836,970 A | 11/1998 | Pandit | |
| 5,900,479 A | 5/1999 | Glasser et al. | |
| 5,919,574 A | 7/1999 | Hoagland | |
| 6,140,089 A | 10/2000 | Aebischer et al. | |
| 6,162,241 A | 12/2000 | Coury et al. | |
| 6,200,595 B1 | 3/2001 | Motoyashiki et al. | |
| 6,344,488 B1 | 2/2002 | Chenite et al. | |
| 6,371,975 B2 | 4/2002 | Cruise et al. | |
| 6,447,802 B2 | 9/2002 | Sessions et al. | |
| 6,458,147 B1 | 10/2002 | Cruise et al. | |
| 6,536,448 B2 | 3/2003 | McDevitt et al. | |
| 6,548,081 B2 | 4/2003 | Sadozai et al. | |
| 6,602,952 B1 | 8/2003 | Bentley et al. | |
| 6,663,653 B2 | 12/2003 | Akerfeldt | |
| 6,706,690 B2 | 3/2004 | Reich et al. | |

(Continued)

FOREIGN PATENT DOCUMENTS

| | | |
|---|---|---|
| EP | 927053 | 4/2003 |
| EP | 1115747 | 2/2004 |

(Continued)

OTHER PUBLICATIONS

Kim, Seung-Ho MD; Stezoski, S. William; Safar, Peter MD; Capone, Antonio MD; Tisherman, Samuel MD. "Hypothermia and Minimal Fluid Resuscitation Increase Survival after Uncontrolled Hemorrhagic Shock in Rats"Journal of Trauma-Injury Infection & Critical Care. 42(2):213-222, Feb. 1997.

(Continued)

*Primary Examiner* — Brian Gulledge
(74) *Attorney, Agent, or Firm* — The Morales Law Firm, LLC; Joseph L. Morales (57) ABSTRACT

A hemostatic putty for treatment of a variety of wounds topographies, including but not limited to highly three dimensional wounds, for example gunshot wounds and impalements, is disclosed. The putty is comprised of a matrix polymer weakly crosslinked or not crosslinked such that a viscoelastic matrix is formed. The viscoelastic nature of the putty is tunable by the composition and enables the putty to conform to a variety of wound topographies. Likewise, a hemostatic polymer, for example chitosan or hydrophobically modified chitosan, is included in this matrix to impart hemostatic properties and tissue adhesive on the putty. The hemostatic polymers disclosed prevent microbial infection and are suitable for oxygen transfer required during normal wound metabolism.

18 Claims, 3 Drawing Sheets

(56) References Cited

U.S. PATENT DOCUMENTS

| | | |
|---|---|---|
| 6,806,260 B1 | 10/2004 | Hirofumi et al. |
| 6,827,727 B2 | 12/2004 | Stalemark et al. |
| 6,830,756 B2 | 12/2004 | Hnojewyj |
| 6,864,245 B2 | 3/2005 | Voumakis et al. |
| 6,890,344 B2 | 5/2005 | Levinson |
| 6,899,889 B1 | 5/2005 | Hnojewyj et al. |
| 6,949,114 B2 | 9/2005 | Hnojewyj et al. |
| 6,958,325 B2 | 10/2005 | Domb |
| 6,967,261 B1 | 11/2005 | Soerens et al. |
| 6,994,686 B2 | 2/2006 | Cruise et al. |
| 6,995,137 B2 | 2/2006 | You et al. |
| 7,019,191 B2 | 3/2006 | Looney et al. |
| 7,041,657 B2 | 5/2006 | Voumakis et al. |
| 7,098,194 B2 | 8/2006 | Chenite et al. |
| 7,115,588 B2 | 10/2006 | Voumakis et al. |
| 7,247,314 B2 | 7/2007 | Hnojewyj et al. |
| 7,279,001 B2 | 10/2007 | Addis et al. |
| 7,288,532 B1 | 10/2007 | Payne et al. |
| 7,318,933 B2 | 1/2008 | Hnojewyj |
| 7,320,962 B2 | 1/2008 | Reich et al. |
| 7,351,249 B2 | 4/2008 | Hnojewyj et al. |
| 7,371,403 B2 | 5/2008 | McCarthy et al. |
| 7,482,503 B2 | 1/2009 | Gregory et al. |
| 7,514,249 B2 | 4/2009 | Gower et al. |
| 7,820,872 B2 | 10/2010 | Gregory et al. |
| 7,897,832 B2 | 3/2011 | McAdams et al. |
| 7,981,872 B2 | 7/2011 | Hardy et al. |
| 8,088,095 B2 | 1/2012 | Hissong et al. |
| 8,106,030 B2 | 1/2012 | Hardy et al. |
| 8,119,780 B2 | 2/2012 | Baker et al. |
| 8,152,750 B2 | 4/2012 | Voumakis et al. |
| 8,269,058 B2 | 9/2012 | McCarthy et al. |
| 8,361,504 B2 | 1/2013 | Hen et al. |
| 8,382,794 B2 | 2/2013 | Belhe et al. |
| 8,414,925 B2 | 4/2013 | Freier |
| 8,481,512 B2 | 7/2013 | Voumakis et al. |
| 8,486,033 B2 | 7/2013 | Orgill et al. |
| 8,530,632 B2 | 9/2013 | Tijsma et al. |
| 8,535,477 B2 | 9/2013 | Ladet et al. |
| 8,536,230 B2 | 9/2013 | Laurencin et al. |
| 8,623,274 B2 | 1/2014 | Kirsch et al. |
| 8,653,319 B2 | 2/2014 | Amery et al. |
| 8,658,193 B2 | 2/2014 | Greenwald |
| 8,658,775 B2 | 2/2014 | Baker et al. |
| 8,664,199 B2 | 3/2014 | Dowling et al. |
| 8,668,899 B2 | 3/2014 | Dowling et al. |
| 8,668,924 B2 | 3/2014 | McCarthy et al. |
| 8,703,170 B2 | 4/2014 | Hedrich et al. |
| 8,703,176 B2 | 4/2014 | Zhu et al. |
| 8,715,719 B2 | 5/2014 | Roorda et al. |
| 8,735,571 B2 | 5/2014 | DeCarlo et al. |
| 8,741,335 B2 | 6/2014 | McCarthy |
| 8,771,258 B2 | 7/2014 | Hedrich et al. |
| 8,795,727 B2 | 8/2014 | Gong et al. |
| 8,802,652 B2 | 8/2014 | Myntti et al. |
| 8,809,301 B2 | 8/2014 | Athanasiadis et al. |
| 8,828,050 B2 | 9/2014 | Gregory et al. |
| 8,835,528 B2 | 9/2014 | Pravata |
| 8,840,867 B2 | 9/2014 | Lerouge et al. |
| 8,920,514 B2 | 12/2014 | Gregory et al. |
| 8,932,560 B2 | 1/2015 | Dowling et al. |
| 8,951,565 B2 | 2/2015 | McCarthy |
| 8,975,387 B1 | 3/2015 | Venditti et al. |
| 8,993,540 B2 | 3/2015 | Haggard et al. |
| 9,004,918 B2 | 4/2015 | McAdams et al. |
| 9,012,429 B2 | 4/2015 | Baker et al. |
| 9,029,351 B2 | 5/2015 | Baker et al. |
| 9,034,379 B2 | 5/2015 | Freier |
| 9,044,488 B2 | 6/2015 | Subramaniam et al. |
| 9,061,087 B2 | 6/2015 | Roberts et al. |
| 9,066,885 B2 | 6/2015 | Raghavan et al. |
| 9,114,172 B2 | 8/2015 | Rhee et al. |
| 9,119,894 B2 | 9/2015 | Huang et al. |
| 9,132,206 B2 | 9/2015 | McCarthy |
| 9,139,664 B2 | 9/2015 | Finkielsztein et al. |
| 9,192,574 B2 | 11/2015 | Medina et al. |
| 9,198,997 B2 | 12/2015 | Myntti et al. |
| 9,205,170 B2 | 12/2015 | Lucchesi et al. |
| 9,226,988 B2 | 1/2016 | Kirsch et al. |
| 9,259,357 B2 | 2/2016 | Kirsch et al. |
| 9,333,220 B2 | 5/2016 | Tijsma et al. |
| 9,364,578 B2 | 6/2016 | Zhu et al. |
| 9,370,451 B2 | 6/2016 | Hardy et al. |
| 9,375,505 B2 | 6/2016 | Hedrich et al. |
| 9,616,088 B2* | 4/2017 | Diehn .................... A61K 38/39 |
| 2002/0028181 A1 | 3/2002 | Miller et al. |
| 2002/0068151 A1 | 6/2002 | Kim et al. |
| 2004/0001893 A1 | 1/2004 | Stupp |
| 2005/0038369 A1 | 2/2005 | Gregory et al. |
| 2005/0147656 A1 | 7/2005 | McCarthy |
| 2005/0181027 A1 | 8/2005 | Messinger |
| 2006/0094060 A1 | 5/2006 | Jarhede et al. |
| 2006/0167116 A1 | 7/2006 | Uchegbu et al. |
| 2006/0269485 A1 | 11/2006 | Friedman et al. |
| 2007/0055364 A1 | 3/2007 | Hossainy |
| 2007/0148215 A1* | 6/2007 | Teslenko ................ A61L 15/28 424/445 |
| 2008/0103228 A1 | 5/2008 | Falcone et al. |
| 2008/0254104 A1 | 10/2008 | Raghavan |
| 2009/0062849 A1 | 3/2009 | Dowling |
| 2009/0192429 A1 | 7/2009 | Daniels et al. |
| 2009/0226391 A1 | 9/2009 | Roberts et al. |
| 2011/0052665 A1 | 3/2011 | Hardy et al. |
| 2011/0217785 A1 | 9/2011 | Liu et al. |
| 2011/0280857 A1* | 11/2011 | Dowling ............ A61L 24/0026 424/94.64 |
| 2012/0058970 A1 | 3/2012 | Dowling |
| 2012/0252703 A1 | 10/2012 | Dowling |
| 2012/0294927 A1* | 11/2012 | Gorka .................... A61L 15/225 424/445 |
| 2014/0275291 A1 | 9/2014 | McGrath et al. |
| 2015/0175714 A1 | 6/2015 | Dowling et al. |
| 2015/0175718 A1 | 6/2015 | Dowling et al. |
| 2016/0213704 A1 | 7/2016 | Dowling et al. |
| 2017/0326169 A1 | 11/2017 | Dowling et al. |
| 2017/0326171 A1 | 11/2017 | Dowling et al. |

FOREIGN PATENT DOCUMENTS

| | | |
|---|---|---|
| EP | 1294414 | 3/2006 |
| EP | 1859816 | 9/2010 |
| EP | 1401352 | 3/2012 |
| EP | 2288744 | 7/2012 |
| EP | 2358412 | 7/2012 |
| EP | 2296637 | 4/2014 |
| EP | 2340002 | 3/2015 |
| EP | 2632502 | 5/2015 |
| EP | 2473203 | 7/2016 |

OTHER PUBLICATIONS

Kjoniksen et al., Light Scattering Study of Semidilute Aqueous Systems of Chitosan and Hydrophobically Modified Chitosans, Macromolecules 31(23):8142-8148 (1998).

Knoll, W.; Frank, C. W.; Heibel, C.; Naumann, R.; Offenhausser, A.; Ruhe, J.; Schmidt, E. K.; Shen, W. W.; Sinner, A. "Functional tethered lipid bilayers." J. Biotechnol. 2000, 74, 137-58.

Koehler et al., Microstructure and Dynamics of Wormlike Micellar Solutions Formed by Mixing Cationic and Anionic Surfactants, J. Phys. Chem. B 104(47):11035-11044 (2000).

Yoshina-Ishii et al. "General Method for Modification of Liposomes for Encoded Assembly on Supported Bilayers." J. Am. Chem. Soc. 2005, 127, 1356-1357.

Kozen, Buddy G. et al., An Alternative Hemostatic Dressing: Comparison of CELOX, HemCon, and QuikClot, Acad. Emerg. Med. 15:74-81(2008).

Kubota, et al. Gelation Dynamics and Gel Structure Fibrinogen, Colloids Surf. B. Biointerfaces 38:103-109 (2004).

Kumar, R.; Raghavan, S. R. "Thermothickening in solutions of telechelic associating polymers and cyclodextrins." Langmuir 2010, 26, 56-62.

(56) References Cited

OTHER PUBLICATIONS

Larson, M. J.; Bowersox, J. C.; Lim, R. C.; Hess, J. R. "Efficacy of a fibrin hemostatic bandage in controlling hemorrhage from experimental arterial injuries." Arch. Surg. 1995, 130, 420-422.
Lee et al., Transition from Unilamellar to Bilamellar Vesicles Induced by an Amphiphilic Biopolymer, Phys. Review Letters, 96:048102-1-048102-4 (2006).
Lee et al., Vesicle-Biopolymer Gels: Networks of Surfactant Vesicles Connected by Associating Biopolymers, Langmuir 21(1):26-33 (2005).
Lew, W. K.; Weaver, F. A. "Clinical use of topical thrombin as a surgical hemostat." Biologics 2008, 2, 593-599.
Li et al., Multivesicular Liposomes for Oral Delivery of Recombinant Human Epidermal Growth Factor, Arch Pharm Res 28(8):988-994 (2005).
Lu, S. et al. "Preparation of Water-Soluble Chitosan" Journal of Applied Polymer Science 91, 3497-2503 (2004).
Lunelli et al., Covalently Anchored Lipid Structures on Amine-Enriched Polystyrene, Langmuir 21(18):8338-8343 (2005).
Macfarlane, R. G. "An enzyme cascade in the blood clotting mechanism, and its function as a biological amplifier." Nature 1964, 202, 498-499.
Malette, William G. et al. Chitosan: A New Hemostatic, The Annals of Thoracic Surgery 36(1):55-58 (1983).
Mansur Yalpani and Laurence D. Hall, Some Chemical and Analytical Aspects of Polysaccharide Modifications. Formation of Branched-Chain, Soluble Chitosan Derivatives, Macromolecules 17(3):272-281 (1984).
Mathivet et al., Shape Change and Physical Properties of Giant Phospholipid Vesicles Prepared in the Presence of an AC Electric Field, Biophysical Journal 70:1112-1121 (1996).
Meier, Wolfgang et al., Vesicle and Cell Networks: Interconnecting Cells by Synthetic Polymers, Langmuir 12:5028-5032 (1996).
Michael I. Fisher and Torbjorn Tjarnhage, Structure and Activity of Lipid Membrane Biosensor Surfaces Studied with Atomic Force Microscopy and a Resonant Mirror, Biosensors & Bioelectronics 15:463-471 (2000).
Naumann et al., Proton Transport Through a Peptide-tethered Pilayer Lipid Membrane by the H+-ATP Synthase from Chloroplasts Measured by Impedance Spectroscopy, Biosensors and Bioelectronics 17:25-34 (2002).
Naumann, C. A.; Prucker, O.; Lehmann, T.; Ruhe, J.; Knoll, W.; Frank, C. W. "The polymer-supported phospholipid bilayer Tethering as a new approach to substrate-membrane stabilization." Biomacromolecules2002, 3, 27-35.
Neuffer, M. C.; McDivitt, J.; Rose, D.; King, K.; Cloonan, C. C.; Vayer, J. S. "Hemostatic dressings for the first responder: A review." Military Med. 2004, 169, 716-720.
New ! Pioneer Chip L1 Improved binding studies in model membrane systems, BIA Journal No. 2 1998.
Nikolelis et al., A Minisensor for the Rapid Screening of Sucralose Based on Surface-stabilized Bilayer Lipid Membranes, Biosensors & Bioelectronics 15:439-444 (2000).
Paul S. Cremer and Steven G. Boxer, Formation and Spreading of Lipid Bilayers on Planar Glass Supports, J. Phys. Chem. B 103(13):2554-2559 (1999).
Pusateri, A. E.; Holcomb, J. B.; Kheirabadi, B. S.; Alam, H. B.; Wade, C. E.; Ryan, K. L. "Making sense of the preclinical literature on advanced hemostatic products." J. Trauma 2006, 60, 674-682.
Puu et al., Retained Activities of Some Membrane Proteins in Stable Lipid Bilayers on a Solid Support, Biosensors and Bioelectronics 10:463-476 (1995).
Raghavan, S. R.; Cipriano, B. H. Gel formation: Phase diagrams using tabletop rheology and calorimetry. InMolecular Gels; Weiss, R. G., Terech, P., Eds.; Springer: Dordrecht, 2005; pp. 233-244.
Rao, S. B.; Sharma, C. P. "Use of chitosan as a biomaterial: Studies on its safety and hemostatic potential."J. Biomed. Mater. Res. 1997, 34, 21-28.
Redepenning, J. et al. "Electrochemical preparation of chitosan/hydroxyapatite composite coatings on titanium substrates." Journal of Biomedical Materials Research. vol. 66A. pp. 411-416. 2003.
Reiss, R. F.; Oz, M. C. "Autologous fibrin glue: Production and clinical use." Transfusion Med. Rev. 1996, 10, 85-92.
Rodriguez, M.S., et al "Interaction between chitosan and oil under stomach and duodenal digestive chemical conditions" Biosci. Biotechnol. Biochem. 69 (11), 2057-2062 (2005).
Rongen et al., Liposomes and Immunoassays, J. Immunol. Methods 204:105-133 (1997).
Tonelli, A. E. "Nanostructuring and functionalizing polymers with cyclodextrins." Polymer 2008, 49, 1725-1736.
Stavroula Sofou and James L. Thomas, Stable Adhesion of Phospholipid Vesicles to Modified Gold Surfaces, Biosensors and Bioelectronics 18:445-455 (2003).
Stewart, R. M.; Myers, J. G.; Dent, D. L.; Ermis, P.; Gray, G. A.; Villarreal, R.; Blow, O.; Woods, B.; McFarland, M.; Garavaglia, J.; Root, H. D.; Pruitt, B. A. "Seven hundred fifty-three consecutive deaths in a level 1 trauma center: the argument for injury prevention." J. Trauma 2003, 54, 66-70.
Szejtli, J. "Introduction and general overview of cyclodextrin chemistry." Chem. Rev. 1998, 98, 1743-1753.
Szymanska et al., Fullerene Modified Supported Lipid Membrane as Sensitive Element of Sensor for Odorants, Biosensors & Bioelectronics 16:911-915 (2001).
Tanaka, M.; Sackmann, E. "Polymer-supported membranes as models of the cell surface." Nature 2005,437, 656-663.
Tangpasuthadol, Surface Modification of Chitosan Films. Effects of Hydrophobicity on Protein Adsorption, Carbohydrate Res. 338:937-942 (2003).
Tanweer A. Khan and Kok Khiang Peh, A Preliminary Investigation of Chitosan Film as Dressing for Punch Biopsy Wound in Rats, J. Pharm. Pharmaceut. Sci. 6(1):20-26 (2003).
U.S. Office Action issued in related U.S. Appl. No. 12/077,173 dated Nov. 8, 2010.
U.S. Office Action issued in related U.S. Appl. No. 12/077,173 dated Apr. 14, 2011.
U.S. Office Action issued in related U.S. Appl. No. 12/231,571 dated Mar. 5, 2012.
U.S. Office Action issued in related U.S. Appl. No. 12/946,818 dated Jan. 28, 2013.
U.S. Notice of Allowance issued in related U.S. Appl. No. 12/946,818 dated Oct. 29, 2013.
U.S. Office Action issued in related U.S. Appl. No. 13/209,399 dated Mar. 1, 2013.
U.S. Office Action issued in related U.S. Appl. No. 13/310,579 dated Apr. 11, 2013.
Zhu et al., Reversible Vesicle Restraint in Response to Spatiotemporally Controlled Electrical Signals: A Bridge between Electrical and Chemical Signaling Modes, Langmuir 23(1) 286-291 (2007).
Whang, Hyun Suk et al., Hemostatic Agents Derived from Chitin and Chitosan, J. Macromolecular Science 45:309-323 (2005).
Wu et al., Spatially Selective Deposition of a Reactive Polysaccharide Layer onto a Patterned Template, Langmuir 19 (3):519-524 (2003).
Wu et al., Voltage-Dependent Assembly of the Polysaccharide Chitosan onto an Electrode Surface, Langmuir 18 (22):8620-8625 (2002).
Yoshina-Ishii et al.,Diffusive Dynamics of Vesicles Tethered to a Fluid Supported Bilayer by Single-Particle Tracking, Langmuir 22(13):5682-5689 (2006).
Zhang, Jing. Drug Delivery: Self-Assembled Nanoparticles based on Hydrophobically Modified chitosan as Carriers for Doxorubicin, Nanomedicine, Elsevier. Aug. 2007. pp. 258-265.
Zhdanov et al. Adsorption and Spontaneous Rupture of Vesicles Composed of Two Types of Lipids (Langmuir 2006, 22, 3477-3480).
Zhdanov et al., Comments on Rupture of Adsorbed Vesicles (Langmuir 2001, 17, 3518-3521).
Zhu et al., Bioinspired Vesicle Restraint and Mobilization Using a Biopolymer Scaffold, Langmuir 22(7):2951-2955 (2006).
"The Hemostatic HemConÂ® Bandage." http://www.hemcon.com/ProductsTechnology/HemConBandageOverview.aspx.

(56) References Cited

OTHER PUBLICATIONS

Alam, Hasan B., et al. Comparative Analysis of Hemostatic Agents in a Swine Model of Lethal Groin Injury, J. Trauma 54:1077-1082 (2003).

Allerbo et al., Simulation of lipid vesicle rupture induced by an adjacent supported lipid bilayer patch (Colloids and Surfaces B: Biointerfaces 2011, 82, 632-636).

Anderluh et al., Properties of Nonfused Liposomes Immobilized on an L1 Biacore Chip and Their Permeabilization by a Eukaryotic Pore-forming Toxin, Anal. Biochem. 344:43-52 (2005).

Angelova, M. I.; Dimitrov, D. S. "Liposome electroformation." Faraday Discuss. 1986, 81, 303-306.

Ankit R. Patel and Curtis W. Frank, Quantitative Analysis of Tethered Vesicle Assemblies by Quartz Crystal Microbalance with Dissipation Monitoring: Binding Dynamics and Bound Water Content, Langmuir 22(18):7587-7599 (2006).

Arnaud, F.; Teranishi, K.; Tomori, T.; Carr, W.; McCarron, R. "Comparison of 10 hemostatic dressings in a groin puncture model in swine." J. Vascular Surg. 2009, 50, 632-639.

Kheirabadi, B. S.; Scherer, M. R.; Estep, J. S.; Dubick, M. A.; Holcomb, J. B. "Determination of Efficacy of New Hemostatic Dressings in a Model of Extremity Arterial Hemorrhage in Swine." J. Trauma 2009, 67, 450-460.

Bochicchio, G.; Kilbourne, M.; Kuehn, R.; Keledjian, K.; Hess, J.; Scalea, T. "Use of a modified chitosan dressing in a hypothermic coagulopathic grade V liver injury model." Am. J. Surg. 2009, 198, 617-622.

Boukobza et al., Immobilization in Surface-Tethered Lipid Vesicles as a New Tool for Single Biomolecule Spectroscopy, J. Phys. Chem. B 105(48):12165-12170 (2001).

Brandenberg, Greg et al. Chitosan: A New Tropical Hemostatic Agent for Diffuse Capillary Bleeding in Brain Tissue, Neurosurgery 15(1): 9-13 (1984).

Burkatovskaya, Marina et al., Use of Chitosan Bandage to Prevent Fatal Infections Developing From Highly Contaminated Wounds in Mice, Biomaterials 27:4157-4164 (2006).

Champion, H. R.; Bellamy, R. F.; Roberts, C. P.; Leppaniemi, A. "A profile of combat injury." J. Trauma2003, 54, S13-S19.

Christensen, S. M.; Stamou, D. "Surface-based lipid vesicle reactor systems: fabrication and applications."Soft Matter 2007, 3, 828-836.

Cenite, A. et al "Rheological characterization of thermogelling chitosan/glycerol-phosphate solutions" Carbohydrate Polymers 46, 39-47 (2001).

Chiaki Yoshina-Ishii and Steven G. Boxer, Arrays of Mobile Tethered Vesicles on Supported Lipid Bilayers, J. Am. Chem. Soc. 125(13):3696-3697 (2003).

Kheirabadi, Bijan S. et al., Hemostatic Efficacy of Two Advanced Dressings in an Aortic Hemorrhage Model in Swine, J. Trauma Injury, Infection, and Critical Care, 59:25-35 (2005).

Cooper et al., A Vesicle Capture Sensor Chip for Kinetic Analysis of Interactions with Membrane-Bound Receptors, Anal. Biochem. 277:196-205 (2000).

Coster, Bag-On-Valve Series Offers Faster Filling and Better Drop Resistance. 2007. Downloaded from the world wide web on Jan. 18, 2012 <http://www.costercom/news/eng/2007-10-18_AE_bov/AE_Manchester_BOV_eng_pdf.>.

D. D. Lasic and D. Papahadjopoulos, Liposomes Revisited, Science 267(5202):1275-1276 (1995).

Dan D. Lasic, Novel Applications of Liposomes, Trens in Biotechnology (TIBTECH) 16:307-321 (1998).

Deng, Y.; Wang, Y.; Holtz, B.; Li, J. Y.; Traaseth, N.; Veglia, G.; Stottrup, B. J.; Elde, R.; Pei, D. Q.; Guo, A.; Zhu, X. Y. "Fluidic and air-stable supported lipid bilayer and cell-mimicking microarrays." J. Am. Chem. Soc2008, 130, 6267-6271.

Desbrieres et al., Hydrophobic Derivatives of Chitosan: Characterization and Rheological Behaviour, Biological Macromolecules, 19:21-28 (1996).

Dimitrievski et al., Influence of Lipid-Bilayer-Associated Molecules on Lipid-Vesicle Adsorption (Langmuir 2010, 26 (8), 5706-5714).

Dimitrievski et al., Simujlations of Lipid Vesicle Adsorption for Different Lipid mixtures (Langmuir 2008, 24, 4077-4091).

Doolittle, R. F. "Fibrinogen and fibrin." Annu. Rev. Biochem. 1984, 53, 195-229.

Dowling, M.B., et al. "A self-assembling hydrophobically modified chitosan capable of reversible hemostatic action." Biomaterials. (May 2011) Vo. 31, pp. 3351-3357.

Durian, Douglas J., et al. "Making a frothy shampoo or beer." Physics Today. pp. 62-63. May 2010.

Eldin, Mohy et al. Chitosan Modified Membranes for Wound Dressing Applications: Preparations, Characterization and Bio-Evaluation. Trend Biomater. Atif.Organs. vol. 22 (3). pp. 158-168.

Ellis-Behnke, R. G.; Liang, Y. X.; You, S. W.; Tay, D. K. C.; Zhang, S. G.; So, K. F.; Schneider, G. E. "Nano neuro knitting: Peptide nanofiber scaffold for brain repair and axon regeneration with functional return of vision."Proc. Natl. Acad. Sci. U. S. A. 2006, 103, 5054-5059.

Ellis-Behnke, R. G.; Liang, Y.-X.; Tay, D. K. C.; Kau, P. W. F.; Schneider, G. E.; Zhang, S.; Wu, W.; So, K.-F. "Nano hemostat solution: Immediate hemostasis at the nanoscale." Nanomedicine 2006, 2, 207-215.

Esquenet et al.,Structural and Rheological Properties of Hydrophobically Modified Polysaccharide Associative Networks, Langmuir 20(9):3583-3592 (2004).

F W Verheugt, M J van Eenige, J C Res, M L Simoons, P W Serruys, F Vermeer, D C van Hoogenhuyze, P J Remme, C de Zwaan, and F Baer. Bleeding complications of intracoronary fibrinolytic therapy in acute myocardial infarction. Assessment of risk in a randomised trial.

Fernandes et al., Electrochemically Induced Deposition of a Polysaccharide Hydrogel onto a Patterned Surface, Langmuir 19(10):4058-4062 (2003).

Fu et al., Protein stability in controlled-release systems, Nature Biotechnology 18:24-25 (2000).

GlaxoSmithKline. Bactroban Ointment: Prescribing Information. Research Triangle Park, NC, May 2005. Downloaded from the world wide web on Jan. 17, 2013 <https://www.gsksource.com/gskprm/htdocs/documents/BACTROAN-OINTMENTS.PDF>.

Gregory F. Payne and Srinivasa R. Raghavan, Chitosan: a Soft Interconnect for Hierarchical Assembly of Nano-scale Components, Soft Matter 3:521-527 (2007).

Kurth, Dirk G. and Thomas Bein. "Monomolecular Layers and Thin Films of Silane Coupling Agents by Vapor-Phase Adsorption on Oxidized Aluminum." J. Phys. Chem. 1992. 96. 6707-6712.

Hirano and Noishiki, The Blood Compatibility of Chitosan and N-Acylchitosans, J. Biochem. Materials Res. 413-417 (1985).

Hou, et al. "Preparation and characterization of RGD-immobilized chitosan scaffolds," Biomaterials 26 (2005) 3197-3206, published Oct. 14, 2004.

Hong et al., Two-step Membrane Binding by Equinatoxin II, a Pore-forming Toxin from the Sea Anemone, Involves an Exposed Aromatic Cluster and a Flexible Helix, J. Biol. Chem. 277(44):41916-41924 (2002).

Hook et al., Supported Lipid Bilayers, Tethered Lipid Vesicles, and Vesicle Fusion Investigated Using Gravimetric, Plasmonic, and Microscopy Techniques, Biointerphases 3(2) (Jun. 2008).

Jung et al., Quantification of Tight Binding to Surface-Immobilized Phospholipid Vesicles Using Surface Plasmon Resonance: Binding Constant of Phospholipase A2, J. Am. Chem. Soc. 122(17):4177-4184 (2000).

Kaler et al., Phase Behavior and Structures of Mixtures of Anionic and Cationic Surfactants, J. Phys. Chem. 96(16): 6698-6707 (1992).

Kaler et al., Spontaneous Vesicle Formation in Aqueous Mixtures of Single-Tailed Surfactants, Science 245(4924): 1371-1374 (1989).

Kauvar, D. S.; Lefering, R.; Wade, C. E. "Impact of hemorrhage on trauma outcome: An overview of epidemiology, clinical presentations, and therapeutic considerations." J. Trauma 2006, 60, S3-S9.

Kean, T.; Thanou, M. "Biodegradation, biodistribution and toxicity of chitosan." Adv. Drug Deliv. Rev. 2010,62, 3-11.

(56) References Cited

OTHER PUBLICATIONS

Chan et al., Mechanical, Bioadhesive Strength and Biological Evaluations of Chitosan Films for Wound Dressing, J. Pharm. Pharmaceut. Sci. 3(3):303-311 (2000).

* cited by examiner

ADVANCED FUNCTIONAL BIOCOMPATIBLE POLYMER PUTTY USED AS A HEMOSTATIC AGENT FOR TREATING DAMAGED TISSUE AND CELLS

CROSSREFERENCE TO RELATED APPLICATIONS

This application claims the priority benefit under 35 U.S.C. § 119(e) of U.S. Provisional Application No. 61/779,706, entitled "ADVANCED FUNCTIONAL BIOCOMPATIBLE POLYMER PUTTY USED AS A HEMOSTATIC AGENT FOR TREATING DAMAGED TISSUE AND CELLS" filed Mar. 13, 2013. This application also claims priority as a continuation from application Ser. No. 14/208,820, entitled "ADVANCED FUNCTIONAL BIOCOMPATIBLE POLYMER PUTTY USED AS A HEMOSTATIC AGENT FOR TREATING DAMAGED TISSUE AND CELLS" filed Mar. 13, 2014, both of which are incorporated herein by reference in their entirety.

BACKGROUND OF THE INVENTION

Field of the Invention

This invention relates to the field of polymer applications for the treatment of wounds.

Background

Around the turn of the new millennium, commercially available hemostatic technologies abruptly changed from ancient to new-age. While cotton gauze had served as the gold standard for treatment of bad bleeds for thousands of years, it was displaced by an arsenal of new materials which had been engineered to rapidly stop bleeding from severe injuries of the extremities. Such technologies were useful to US soldiers in both Operation Iraqi Freedom and Operation Enduring Freedom. The key products contracted to the military include 1) Quikclot® (a registered trademark of Z-MEDICA, LLC) Combat Gauze, a gauze impregnated with kaolin nanoparticle powder which absorbs large amounts of water and hence concentrates clotting factors, 2) the Hemcon Patch® (a registered trademark of HemCon Medical Technologies, Inc.), a freeze-dried bandage composed of chitosan, a material extracted from shrimp shells, and 3) Woundstat® (a registered trademark of TraumaCure, Inc.), a clay mineral-based powder which, like Quikclot, absorbs high volumes of fluid quickly.

Although these products typically have done an adequate job of treating bleeding from extremities or superficial wounds in combat, they all have significant drawbacks. For example, Quikclot nanoparticles and Woundstat granules are very difficult to remove once an injured soldier arrives at a medical facility; this can cause permanent tissue scarring and/or peripheral clotting. Furthermore, these powders also pose a liability of blowing into the eyes of soldiers and medics in the field. The Hemcon Bandage is relatively easy to remove, but it offers little flexibility in application due to the preformed shape of the solid bandage. Combat Gauze, and other gauze types, requires significant manual packing and compression times which put the lives of field medics at significant risk, particularly when under fire. Indeed, the salient common denominator among all currently available hemostats is the requirement for sustained compression. It is also worth noting that even with sustained compression on the bleeding site, such products demonstrate only mediocre effectiveness in treating severe life-threatening bleeds on the battlefield.

Like the solid, compressible products (gauze, bandage, powder) described above, countless other related technologies have also been developed over the last decade using essentially the same form factors and raw materials, with only incremental (or ambiguous) improvements demonstrated in pre-clinical studies. As such, a need exists for a hemostatic material which is easily packable and requires no sustained compression time. Of course, this material also should be highly effective, safe, low cost, durable and easily removable for it to be useful to military and civilian emergency medics.

SUMMARY OF THE INVENTION

A composition of matter for use in healing wounds and stopping hemorrhage is described in this application. The composition of matter has four components: a hemostatic biopolymer, a secondary polymer, an ionic crosslinker, and a solvent. The hemostatic biopolymer may be a chitosan, alginate, cellulosic or a polypeptide capable of assisting in the treatment of wounds and hemorrhage. The hemostatic biopolymer in some instances may be a hydrophobically modified chitosan. The secondary biopolymer may be a large molecular weight polymer, such as polyvinyl alcohol. The crosslinker in some embodiments is sodium borate, a weak crosslinker.

In other embodiments, the hybrid composition of matter is used in a method for controlling bleeding. In yet other embodiments, the composition of matter is part of a kit for application of the composition of matter to a wound.

It is to be understood that both the foregoing general description and the following detailed description are exemplary and explanatory only and are not restrictive of the invention as claimed. The accompanying drawings, which are incorporated in and constitute a part of the specification, illustrate an embodiment of the invention and together with the general description, serve to explain the principles of the invention.

BRIEF DESCRIPTION OF THE DRAWINGS

The above and other features, aspects, and advantages of the present invention are considered in more detail, in relation to the following description of embodiments thereof shown in the accompanying drawings, in which.

DETAILED DESCRIPTION OF THE INVENTION

The invention summarized above may be better understood by referring to the following description, which should be read in conjunction with the accompanying claims and drawings in which like reference numbers are used for like parts. This description of an embodiment, set out below to enable one to build and use an implementation of the invention, is not intended to limit the invention, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent constructs and cell lines do not depart from the spirit and scope of the invention in its broadest form.

Hybrid Composition of Matter of Putty

In this application the term "hemostat" means a composition of matter, such as a polymer putty, that adheres to tissues and forms aggregates with blood cells and blood cell clots, assisting in the clotting process and effectively stopping hemorrhage. As utilized here, the term "aggregate" refers to the hydrophobic interactions between the red blood cells and a hydrophobically modified biopolymer and interactions with other components of the composition of matter that assist in the control of hemorrhage.

The term "hydrophobically modified biopolymer" refers to a synthetic or naturally occurring polysaccharide or peptide; where the hydrophobic modification consists of the covalent binding of hydrophobic substituents to the polymer backbone. The manufacture and composition of the hydrophobically modified biopolymer is described in U.S. Pat. Nos. 8,664,199 and 8,668,899; and also in U.S. Application Publication Nos. US2008/0254104A1, US2009/0062849A1, and US2012/0252703A1, all of which are incorporated herein by reference in their entireties.

A hybrid composition of matter that provides a moldable and adhesive hemostatic agent comprises at least four components: (1) a hemostatic biopolymer; (2) a secondary polymer matrix; (3) a crosslinker, and (4) a solvent. The combination of these elements forms a "putty," which in this application refers to a composition of matter with sufficient viscosity and hemostatic activity to assist in controlling bleeding and hemorrhage.

The hemostatic biopolymer may comprise a hydrophobically modified biopolymer matrix capable of hydrophobically interacting with tissue, particularly hemostatic interaction with damaged tissue. In some embodiments, the hemostatic polymer is comprised of at least one polymer and a plurality of short hydrophobic substituents attached along the backbone of the polymer. In other embodiments, the hemostatic biopolymer is not hydrophobically modified. The polymer is either synthetic or naturally occurring, including for example, water-soluble polysaccharides and water-soluble polypeptides. For example, the polymer is one or more hydrophobically modified polysaccharides selected from the group consisting of chitosans, alginates, cellulosics or gelatins.

All four types of materials allow for the transfer of oxygen and moisture required to metabolize the wound healing physiology. Chitosan also has inherent anti-microbial properties; this is a crucial asset for materials covering open wounds because it eliminates the need to constantly change wound dressings in order to disinfect the wound manually between changes. Positive charges along the backbone of chitosan cause it to interact electrostatically with negatively charged blood cells, thus creating a sticky interface between the putty and the wound. Chitosan provides hemostasis for a period of about 30 min before becoming saturated with blood cells and losing adhesion to the wound site. Hydrophobically-modified (hm)-chitosan, in particular, has been shown to increase the tissue adhesion properties of materials in which it is incorporated. Here, too, the addition of hm-chitosan into a PVA-Borax putty increases the overall adhesive properties of the putty. Adhesiveness of the putties can be tuned by the amount of hm-chitosan included in the blend relative to PVA-Borax, or by the level of hydrophobic modified to the hm-chitosan molecule itself.

Chitosans (whether modified or unmodified) include, for example, the following chitosan salts: chitosan lactate, chitosan salicylate, chitosan pyrrolidone carboxylate, chitosan itaconate, chitosan niacinate, chitosan formate, chitosan acetate, chitosan gallate, chitosan glutamate, chitosan maleate, chitosan aspartate, chitosan glycolate and quaternary amine substituted chitosan and salts thereof, etc. Alginates (whether modified or unmodified) include, for example, sodium alginate, potassium alginate, magnesium alginate, calcium alginate, aluminum alginate, etc. Cellulosics include, for example, hydroxyetyhl cellulose, hydroxypropyl cellulose, methyl cellulose, hydroxypropyl methyl cellulose, hydroethyl methyl cellulose, etc. In an example, the polymeric component of the hemostat comprises mixtures of polysaccharides between classes, e.g., cellolusics and chitosans, or within the same class, e.g., two different types of alginate.

The polymeric components suitable for use in the hybrid composition can comprise one or more hydrophobically modified polysaccharide selected from the group consisting of cellulosics, chitosans and alginates. Such polysaccharide starting materials from which the hydrophobically modified polysaccharides can be made are known to those skilled in the art. Cellulosics, chitosans and alginates are all abundant, natural biopolymers. Cellulosics are found in plants, whereas chitosans and alginates are found in the exoskeleton or outer membrane of a variety of living organisms. All three types of materials allow for the transfer of oxygen and moisture required to metabolize the wound healing physiology.

Gelatins are polypeptides derived from the skin and bones of mammals. These polypeptides are degraded forms of their pre-cursor protein, collagen. Gelatin is a thermo-reversible biopolymer which undergoes a phase transition from solid to liquid above 32° C. at concentrations of 3 wt % or greater in water. Preferred sources of gelatin include gelatin from bovine skin, gelatin from bovine bones, gelatin from porcine skin and gelatin from porcine bones. These polypeptides display excellent biocompatibility and resorption characteristics.

The second component of the putty is a secondary polymer matrix. In a preferred embodiment, the secondary polymer matrix is a polyvinyl alcohol (PVA) in the molecular weight range of 125,000 Da to 140,000 Da. In a further embodiment, the PVA is in the molecular weight range of 50,000 Da to 125,000 Da. In another further embodiment, the PVA is in the molecular weight range of 140,000 Da to 300,000 Da. In such exemplary embodiment, the secondary polymer can be included in concentration of between 5 wt % and 15 wt %. In a preferred embodiment, the level of hydrolysis of the PVA is in a range from 70% to 100% hydrolyzed. In a further embodiment, the level of hydrolysis of the PVA is in a range from 30% to 70%. A crosslinker, sodium tetraborate decahydrate, is included in the blend at a concentration of between 0.1 wt % and 1.0 wt %. The hemostatic polymer, chitosan or hydrophobically-modified chitosan, is included in the putty blend a concentration of between 0.1 wt % and 3 wt %. It is contemplated that the crosslinker may include sodium tetraborate decahydrate, or other borate salts, such as sodium perborate or sodium metaborate. When a crosslinker is present, the crosslinker interacts with the secondary polymer based upon hydrogen bonding or ionic weak interactions. For example, when borate salts are used as a crosslinker, di-diol interactions with the matrix polymer assist in enhancing the viscoelasticity of the hybrid composition. Such interactions are present in compositions without a crosslinker, but addition of the crosslinker helps enhance these properties. The weak interaction between the polymer chains results in the viscoelastic character of the putty that enables it to conform to highly three-dimensional wounds. Likewise, the viscoelastic character may be tuned by varying polymer molecular weight, polymer concentration, crosslinker type, or concentration of crosslinker. The putty may be comprised of entirely matrix polymer with the hemostatic polymer as an additive or it may be comprised of the matrix polymer in a solvent, for example water or organic solvents.

The ratio of the liquid and solid-like character of the putty can be tuned through the use of different polymer concentrations, polymer molecular weights, type of ionic cross linker, or concentration of ionic cross linker. For example, the putty may be in the form of a very viscous fluid, but one that is still capable of being injected from a medical syringe into very narrow wounds, such as gunshot or impalement wounds. Likewise, the putty may take the form of a higher modulus, solid-like pad for shallower wounds. Note that the solid-like putty will still deform over time to conform to the three-dimensional topography of the wound. Additionally, the weak crosslinking nature of the putty enables it to swell when in contact with wound exudate. This swelling action of the putty can provide a compressive force normal to the wound surface when placed into a confined wound cavity. In a preferred embodiment the compressive force is between 5 and 15 N. In a further embodiment the compressive force is between 15 and 30 N. In a further preferred embodiment, the compressive force is between 0.1 and 5 N.

The weakly cross-linked polymer matrix has both viscous properties of a liquid (i.e. it flows if left for long times on a surface) and elastic properties of a solid (i.e. it can be bounced off of a surface like a rubber ball) and thus can be termed viscoelastic (having both liquid and solid character). This viscoelastic character enables the putty to conform to the three-dimensional topography of wounds to ensure intimate contact of the hemostatic polymer agent and the surface of the wound. Likewise, the solid-like nature of the material enables the putty to transmit external compressive force to the interior surfaces of the wound.

The fourth component of the hybrid composition of matter consists of a solvent. In some preferred embodiments, the solvent is water.

In one preferred embodiment, the composition of matter, putty, is composed of a (1) hydrophobically modified biopolymer matrix capable of hydrophobically interacting with tissue, particularly hemostatic interaction with damaged tissue, (2) polyvinyl alcohol (PVA) or polyvinyl acetate, (3) a borate salt, such as sodium tetraborate decahydrate, and (4) water.

Method of Manufacturing Hybrid Composition of Matter of Putty

The putty, or hybrid composition, is manufactured by adding the hemostatic polymer to the secondary matrix polymer, in some cases one or both may be dissolved in solvent, and adding the crosslinker to the polymer mixture. In a preferred embodiment, the secondary matrix polymer is PVA. The PVA is dissolved in water by heating at 95° C. for 15 minutes under stirring. The PVA is then cooled to room temperature and mixed with the hemostatic polymer and the crosslinker. This mixture is then stirred or kneaded for 15 minutes to 60 minutes to mix the components and entangle the matrix polymer chains until yielding a viscoelastic putty.

In another embodiment, the putty material may be made of such viscosity that it can be used as a hemostatic pad for topical application on wounds. The putty should be soft enough that it can be shaped to appropriate size and may conform closely to the three dimensional topography of the wound, but solid enough that it can withstand the force of compression from the individual administering treatment to the wound and that it can transmit this compressive force to the surface of the wound.

In one exemplary method, the hydrophobically modified polymer is manufactured, where the hydrophobic modifications consist of the addition of hydrophobic substituents to the polymer's backbone. In one example, a hydrophobic substituent comprising a hydrocarbon group having from about 8 to about 18 carbon atoms is attached to the backbone of the at least one polysaccharide. In an example, the hydrocarbon group comprises an alkyl or arylalkyl group. As used herein, the term "arylalkyl group" means a group containing both aromatic and aliphatic structures. Procedures for hydrophobically modifying the above mentioned polysaccharides are described in U.S. Pat. Nos. 8,664,199 and 8,668,899; and also in United States Application Publication Numbers US2008/0254104A1, US2009/0062849A1, and US2012/0252703A1, all of which are incorporated herein by reference in their entireties.

In one embodiment of the present hemostatic composition, the degree of substitution of the hydrophobic substituent on the polysaccharide is from about 1 to about 100 moles of the hydrophobic substituent per mole of the polysaccharide. In an example, more than one particular hydrophobic substituent is substituted onto the polysaccharide, provided that the total substitution level is substantially within the ranges set forth above. In a further preferred embodiment, the degree of substitution of the hydrophobic substituent on the polysaccharide is from about 40 to 65 moles of the hydrophobic substituent per mole of the polysaccharide. In another preferred embodiment, the molecular weight of the polysaccharides used as the hemostatic polymer range from about 50,000 to about 1,500,000 grams per mole. In examples, the molecular weight of the polysaccharides comprising the spray ranges from about 50,000 to about 25,000 grams per mole. As used herein, the term "molecular weight" means weight average molecular weight. The preferred methods for determining average molecular weight of polysaccharides are low angle laser light scattering (LLS) and Size Exclusion Chromatography (SEC). In performing low angle LLS, a dilute solution of the polysaccharide, typically 2% or less, is placed in the path of a monochromatic laser. Light scattered from the sample hits the detector, which is positioned at a low angle relative to the laser source. Fluctuation in scattered light over time is correlated with the average molecular weight of the polysaccharide in solution. In performing SEC measurements, again a dilute solution of polysaccharide, typically 2% or less, is injected into a packed column. The polysaccharide is separated based on the size of the dissolved polysaccharide molecules and compared with a series of standards to derive the molecular weight.

In an example, the putty material is mixed with a variety of water-soluble reagents that result in faster and more efficient healing of the wound. A first class of reagents that is mixed with the hydrophobically modified polysaccharide is comprised of those reagents that contribute to the hemostatic integrity of the clot such as for example human thrombin, bovine thrombin, recombinant thrombin, and any of these thrombins in combination with human fibrinogen. Other examples of the first class of reagents include fibrinogen, Factor VIIa, and Factor XIII. A second class of reagents that is mixed with the hydrophobically modified polysaccharide is comprised of those reagents that prevent microbial infection such as norfloxacin (anti-microbial), silver (anti-microbial), ampicillin (antibiotic) and penicillin (antibiotic) Reagents from both classes, e.g. recombinant thrombin and norfloxacin, or reagents from the same class, e.g. recombinant thrombin and fibrinogen, may be mixed with the polysaccharide.

The hydrophobically modified polymer is combined with the secondary polymer matrix and a solvent. In a preferred embodiment, the secondary polymer matrix is a polyvinyl alcohol (PVA) in the molecular weight range of 125,000 Da to 140,000 Da. In such exemplary embodiment, the secondary polymer can be included in concentration of between 5 wt % and 15 wt %. The level of hydrolysis of the PVA may range from 70% to 100% hydrolyzed. A crosslinker, sodium tetraborate decahydrate, is included in the blend at a concentration of between 0.1 wt % and 1.0 wt %. The hemostatic polymer, chitosan or hydrophobically-modified chitosan, is included in the putty blend a concentration of between 0.1 wt % and 3 wt %.

Methods of Utilizing the Hybrid Composition of Matter of Putty

In one embodiment of the present invention, a hemostatic composition and delivery system is used for treating both compressible and non-compressible hemorrhages effectively. Many different types of materials and syringe devices can be used. For surgical or medical field use, however, it can be desirable to sterilize the composition and the syringe device using autoclave, gamma-irradiation, electron beam irradiation or sterile ultrafiltration.

The composition can be used in a method for treating compressible and non-compressible hemorrhages through use of a hemostat. The putty is applied to a wound to stop bleeding and hemorrhage. The hemostatic putty, or polymer dough, is suitable for use in mammals. As used herein, the term "mammals" means any higher class of vertebrates that nourish their young with milk secreted by mammary glands, e.g. humans, rabbits and monkeys.

It is contemplated that this putty may be included as part of a syringe delivery system as may be known by those skilled in the art. The hemostatic interaction occurs through application of the moldable putty into an injured tissue site and subsequent process wherein a plurality of short hydrophobic substituents, that are attached with the biopolymer backbone, interact with and adhere to blood and tissue upon swelling of the putty.

In another embodiment, the putty material may be made of such viscosity that it may be pumped through a syringe into a deep wound cavity, such as a gunshot wound or impalement wound. The syringe here refers to any device that applies pressure to the viscoelastic fluid such that is flows out of the narrow tip of the device, thus enabling application of the putty to the wound. The putty, having been applied the wound, may be left alone to swell in the wound or may receive additional compression from the external part of the wound to aid in clot formation. After achieving hemostasis, the putty may be removed from the cavity as a single wound dressing.

Kits Comprising the Hybrid Composition of Matter of Putty

Figure 6:
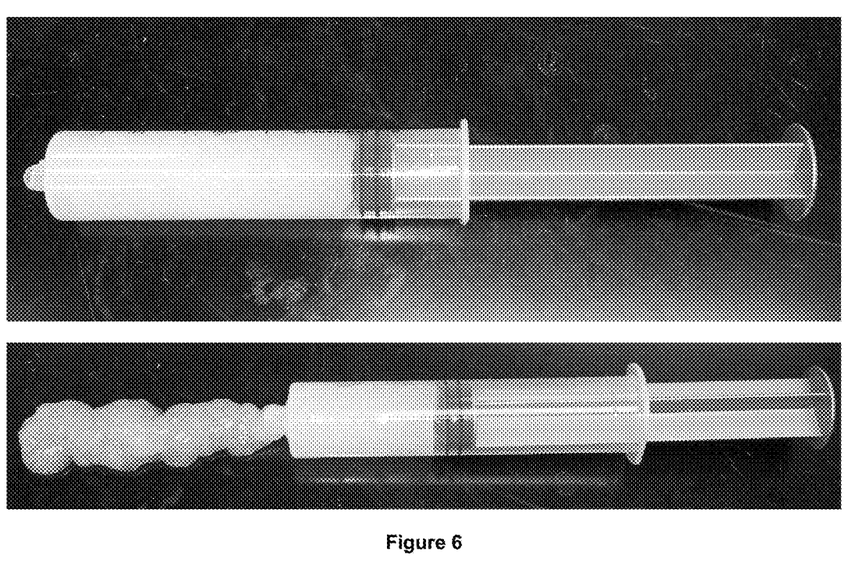
FIG. 6 shows a diagram of a syringe wherein the composition of matter is contained as a kit for application to a wound.

One embodiment of the present invention, a kit for treating wounds is provided comprising a container with a hybrid composition described herein and an applicator. The applicator can be a syringe or any other type of apparatus known to a person of ordinary skill in the art to apply a semiliquid to an intended area, such as a wound. In one example, the kit consists of a pre-packed syringe containing a particular formulation of the putty and ready for use as shown in FIG. 6.

EXAMPLE 1

Figure 1:
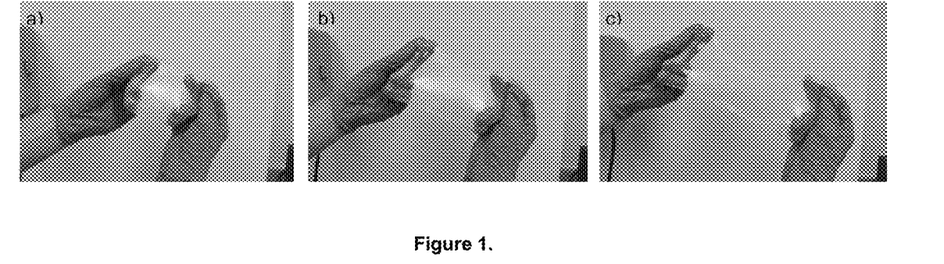
FIG. 1 shows a demonstration of viscoelastic form factor of polyvinyl alcohol-borate-chitosan putty is shown. The putty is elastic (solid-like) enough to be held in the hand, but the putty is viscous (liquid-like) enough to be molded and stretched to various shapes to fit wounds and will conform to any wound topography.
Figure 2:
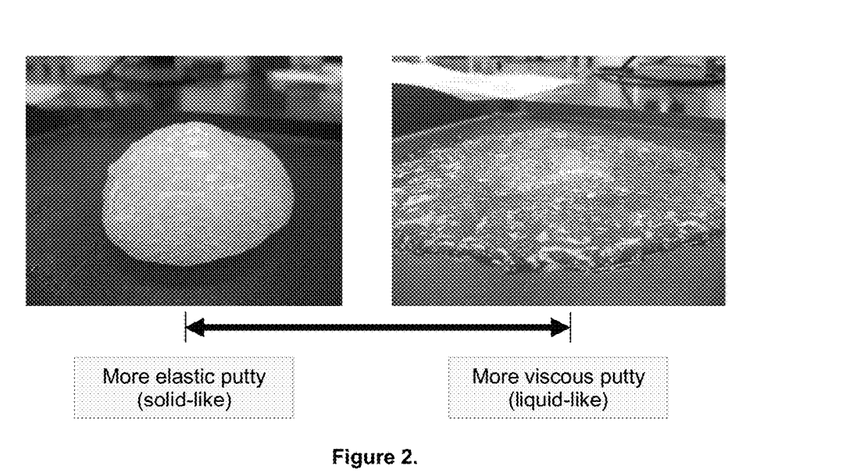
FIG. 2 shows an example putty (polyvinyl alcohol-borate-chitosan) can be tuned to have specific viscous and elastic properties by modifying polymer concentration, polymer molecular weight, crosslinker type, and crosslinker concentration. Here the polymer concentration is varied from about 12 wt % (a) to 7 wt % (b) with a borate crosslinker at a 1:40 mass ratio of the polymer. The chitosan concentration is 1 wt % in both 2 (a) and 2 (b).

As shown in FIG. 1, the hybrid composition putty described here has viscoelastic properties that are useful in treating acute wounds. The Figure shows how the composition can be manipulated easily to change its shape and be stretched significantly. The example in FIG. 2 shows the change in elasticity of the putty depending on the concentration of polymer used. Here the polymer concentration is varied from about 12 wt % (a) to 7 wt % (b) with a borate crosslinker at a 1:40 mass ratio of the polymer. The chitosan concentration is 1 wt % in both 2 (a) and 2 (b).

Figure 3:
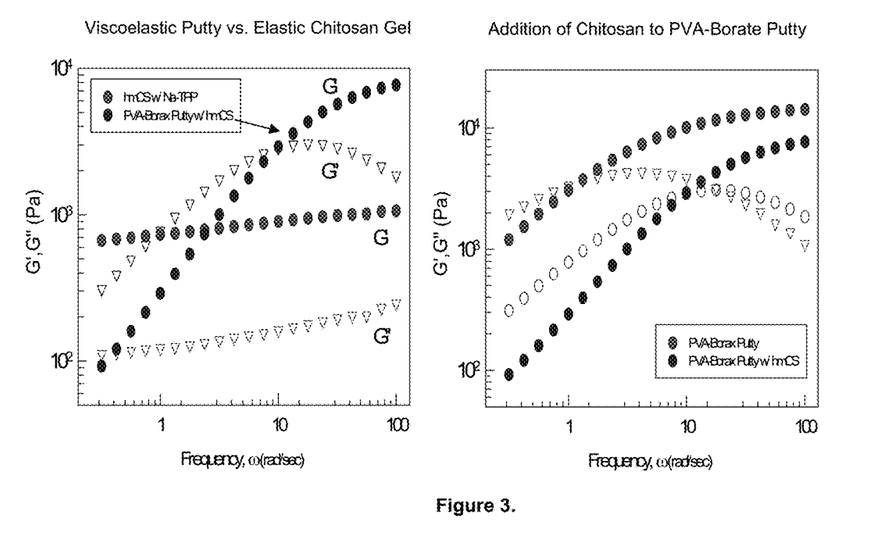
FIG. 3 shows (a) dynamic rheology of a viscoelastic putty consisting of polyvinyl alcohol crosslinked with sodium borate (PVA-Borax) blended with hydrophobically-modified chitosan (hmCS) (upper curves) vs. an hmCS sample crosslinked with sodium tripolyphosphate (NaTPP) (lower curves) and (b) dynamic rheology of a polyvinyl alcohol-borate putty (upper curves) and of a PVA-Borax putty with hemostatic polymer, hmCS, added (lower curves).

Rheological Experiments: Steady shear rheological experiments were performed on a Rheometrics AR2000 stress-controlled rheometer. A cone-and-plate geometry of 40 mm diameter and 4° cone angle was used and samples were run at the physiological temperature of 37° C. Data on the same samples via dynamics rheology are shown in FIG. 3 where the elastic (G') and viscous (G") moduli are plotted as a function of frequency (rad/s) of oscillatory shear. Here, we note that the putty sample has a transition in elastic-like behavior (G'>G") to viscous-like behavior (G">G') over long time scales.

Figure 4:
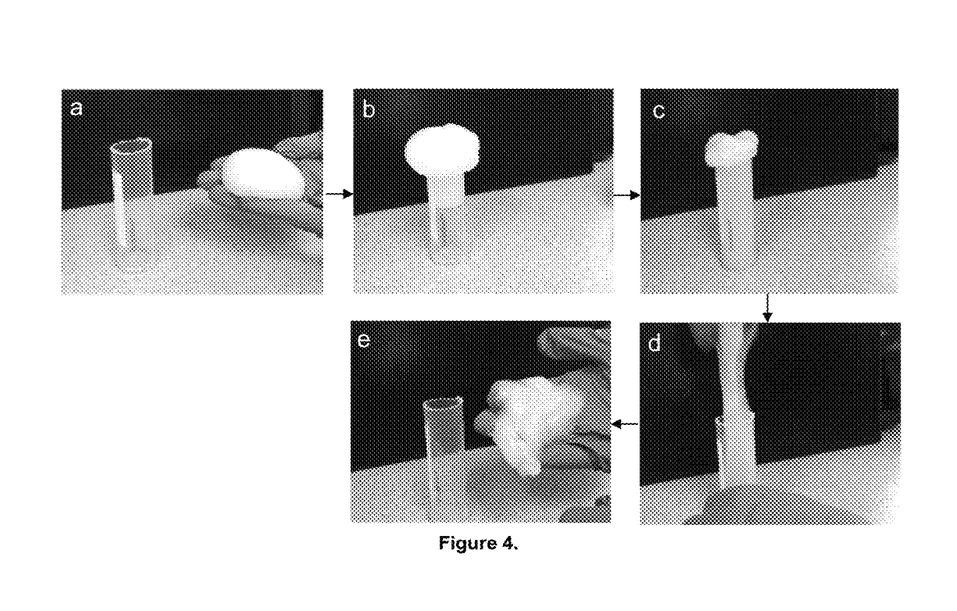
FIG. 4 shows an example putty, polyvinyl alcohol crosslinked with sodium borate (PVA-Borax) blended with hydrophobically-modified chitosan (hmCS), (a) can be easily inserted into a simulated three-dimensional wound (b), holds its own weight (c), and be removed entirely from the cavity (d-e).
Figure 5:
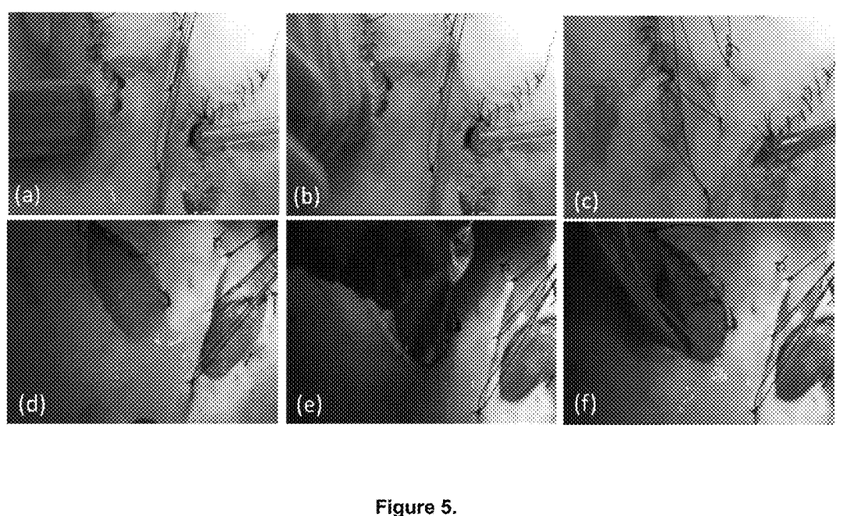
FIG. 5 shows an in vivo application of hemostatic putty to porcine arterial 5-French laceration (gunshot model). In (a), a 60 cc syringe loaded with putty, consisting of polyvinyl alcohol crosslinked with sodium borate (PVA-Borax) blended with hydrophobically-modified chitosan (hmCS), is positioned near an aperture above the artery. In (b), the putty is syringed into the bleeding cavity through the aperture. In (c), the delivered putty is observable at the aperture. Next in (d), the aperture is widened to observe hemostasis in the cavity filled with putty. Finally, in (e) and (f) the putty is removed by hand, with no re-bleeding observed.

The putty or hybrid composition of described in here has been shown to work in simulated three-dimensional wounds as shown in FIG. 4. The putty has been shown to be easily applied and removed from such simulated wounds. The putty has also been used in vivo as shown in FIG. 5. The experimental design for this in vivo application is as follows. Female Yorkshire pigs, weighing 39.2±2.3 kg (n=3) were obtained from the Knight Surgical Lab at Massachusetts General Hospital (Boston, Mass.). All animals were maintained in a facility accredited by the Association for Assessment and Accreditation of Laboratory Animal Care, and all experiments were performed in accordance with the National Research Council's Guide for the Care and Use of Laboratory Animals. The protocol was approved by the IACUC at Massachusetts General Hospital. The swine were anesthetized with 6 mg/kg of telazol and 0.01 mg/kg of glycopyrrolate that were given intramuscularly. They were incubated and placed on mechanical ventilation at a tidal volume 12 mL/kg, a rate of 10 respirations per minute, and 100% oxygen. Anesthesia was maintained using isoflurane, and ventilatory parameters were maintained to attain an end-tidal $CO_2$ partial pressure of 40 mm Hg.

To create a hemorrhage in the groin area, approximately 5 cm of the right femoral artery was dissected free from surrounding tissues and the overlying abductor muscle was removed. A 5 French catheter was inserted into the artery. Next, the skin above the artery was sutured closed, with the exception of a small aperture approximately 2 cm in diameter. Finally, the catheter was pulled from the artery to create hemorrhage.

In (a), a 60 cc syringe loaded with putty, consisting of polyvinyl alcohol crosslinked with sodium borate (PVA-Borax) blended with hydrophobically-modified chitosan, is positioned near an aperture above the femoral artery. Once the catheter was removed from the artery, significant bleeding within the cavity occurred. A small hole in the skin remained the only access point to the bleed. Compressible devices such as bandages and gauze were not able to be applied through the hole. In (b), the putty is syringed into the bleeding cavity through the aperture after 1 minute of free bleeding. In (c), the delivered putty is observable at the aperture. Next in (d), the aperture is widened to observe hemostasis in the cavity filled with putty. Finally, in (e) and (f) the putty is removed by hand after 30 min, with no re-bleeding observed.

The invention has been described with references to a preferred embodiment. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

What is claimed is:

1. A putty, comprising:
   a hemostatic biopolymer selected from hydrophobically modified alginate and hydrophobically modified gelatin,
   a secondary polymer, and wherein the secondary polymer is polyvinyl alcohol
   an ionic crosslinker, and
   a solvent.

2. The putty of claim 1, wherein the hydrophobically modified biopolymer comprises hydrophobic substituents covalently attached to the biopolymer.

3. The putty of claim 2, wherein the hydrophobic substituents comprise from eight to eighteen carbon atoms.

4. The putty of claim 3, wherein the hydrophobic modification is of 1 to 100 moles of hydrophobic substituent per 1 mole of biopolymer.

5. The putty of claim 1, wherein the hydrophobically modified alginate is selected from the group consisting of sodium alginate, potassium alginate, magnesium alginate, calcium alginate, aluminum alginate.

6. The putty of claim 1, wherein the polyvinyl alcohol is present in a concentration of between 5 wt % and 15 wt %.

7. The putty of claim 6, wherein the polyvinyl alcohol has a molecular weight in of between 50,000 Da and 300,000 Da.

8. The putty of claim 6, wherein the polyvinyl alcohol has a molecular weight in of between 125,000 Da and 140,000 Da.

9. The putty of claim 6, wherein the polyvinyl alcohol is hydrolyzed in a range of 70% to 100%.

10. The putty of claim 1, wherein the crosslinker is present in a concentration of between 0.1 wt % and 1.0 wt %.

11. The putty of claim 1, wherein the hemostatic biopolymer is present in a concentration of between 0.1 wt % and 3.0 wt %.

12. The putty of claim 1, wherein the composition of matter is capable of providing a compressing force of between 5 and 15 N, 15 and 30 N, or 0.1 and 5N.

13. The putty of claim 1, where in the crosslinker is a borate salt.

14. The putty of claim 13, wherein the borate salt is selected from the group consisting of sodium tetraborate decahydrate, sodium peroborate, and sodium metaborate.

15. The putty of claim 1, further comprising a water soluble reagent.

16. The putty of claim 15, wherein the water soluble reagent selected from the group consisting of human thrombin, bovine thrombin, recombinant thrombin, and human fibrinogen.

17. The putty of claim 1, further comprising a reagent selected from the group consisting of fibrinogen, factor VIIa, Factor XIII.

18. The putty of claim 1, further comprising a reagent that prevent microbial infections.

* * * * *